United States Patent
Yasuno et al.

(10) Patent No.: US 11,759,104 B2
(45) Date of Patent: Sep. 19, 2023

(54) SCANNING IMAGING APPARATUS, METHOD OF CONTROLLING THE SAME, SCANNING IMAGING METHOD, AND RECORDING MEDIUM

(71) Applicants: University of Tsukuba, Ibaraki (JP); TOPCON CORPORATION, Tokyo (JP)

(72) Inventors: Yoshiaki Yasuno, Tsukuba (JP); Shuichi Makita, Tsukuba (JP); Tatsuo Yamaguchi, Warabi (JP); Toshihiro Mino, Warabi (JP)

(73) Assignees: UNIVERSITY OF TSUKUBA, Ibaraki (JP); TOPCON CORPORATION, Tokyo (JP)

( * ) Notice: Subject to any disclaimer, the term of this patent is extended or adjusted under 35 U.S.C. 154(b) by 437 days.

(21) Appl. No.: 17/013,695

(22) Filed: Sep. 7, 2020

(65) Prior Publication Data

US 2021/0068651 A1 Mar. 11, 2021

(30) Foreign Application Priority Data

Sep. 10, 2019 (JP) ................................. 2019-164245

(51) Int. Cl.
*A61B 3/00* (2006.01)
*A61B 3/10* (2006.01)
*G01B 9/02091* (2022.01)

(52) U.S. Cl.
CPC ............ *A61B 3/102* (2013.01); *A61B 3/0025* (2013.01); *G01B 9/02091* (2013.01)

(58) Field of Classification Search
CPC ..... A61B 3/0025; A61B 3/102; A61B 3/1025; G01B 2290/65; G01B 9/02004; G01B 9/02077; G01B 9/02091
See application file for complete search history.

(56) References Cited

U.S. PATENT DOCUMENTS

2013/0301008 A1 11/2013 Srivastava et al.
2016/0317029 A1 11/2016 Srivastava et al.
(Continued)

FOREIGN PATENT DOCUMENTS

JP 2015-515894 A 6/2015
JP 2015-221091 A 12/2015
(Continued)

OTHER PUBLICATIONS

Chen, Y., et al., "Three-dimensional eye motion correction by Lissajous scan optical coherence tomography," Biomedical Optics Express, vol. 8, No. 3, Mar. 1, 2017, pp. 1783-1802.
(Continued)

*Primary Examiner* — Mark D Remaly
(74) *Attorney, Agent, or Firm* — XSENSUS LLP

(57) ABSTRACT

In a scanning imaging apparatus of some aspect examples, a scanner applies an optical scan to a sample to acquire data. A scan controller controls the scanner to sequentially apply, to the sample, pattern scans according to a two-dimensional pattern including cycles. A movement unit relatively moves a scan area corresponding to the two-dimensional pattern and the sample. A movement controller controls the movement unit such that cycles in first and second scans of the pattern scans cross each other. An image constructing unit constructs an image based on data acquired under controls performed by the scan controller and the movement controller. The scan controller and the movement controller perform controls of the scanner and the movement unit respectively such that first and second cycles in a pattern scan cross each other at least at one point.

13 Claims, 13 Drawing Sheets

(56) References Cited

U.S. PATENT DOCUMENTS

| | | |
|---|---|---|
| 2017/0065171 A1 | 3/2017 | Satake et al. |
| 2018/0242839 A1 | 8/2018 | Fukuhara et al. |

FOREIGN PATENT DOCUMENTS

| | | |
|---|---|---|
| JP | 2016-017915 A | 2/2016 |
| JP | 2016-077506 A | 5/2016 |
| JP | 2017-047113 A | 3/2017 |
| JP | 2017-086311 A | 5/2017 |
| JP | 2018-068578 A | 5/2018 |
| JP | 2018-140004 A | 9/2018 |
| JP | 2018-140049 A | 9/2018 |

OTHER PUBLICATIONS

Chen, Y., et al., "Eye-motion-corrected optical coherence tomography angiography using Lissajous scanning," Biomedical Optics Express, vol. 9, No. 3, Mar. 1, 2018, pp. 1111-1129.

Japan Office Action dated Mar. 28, 2023 in corresponding Japanese Patent Application No. 2019-164245 (with machine-generated English translation), 6 pages.

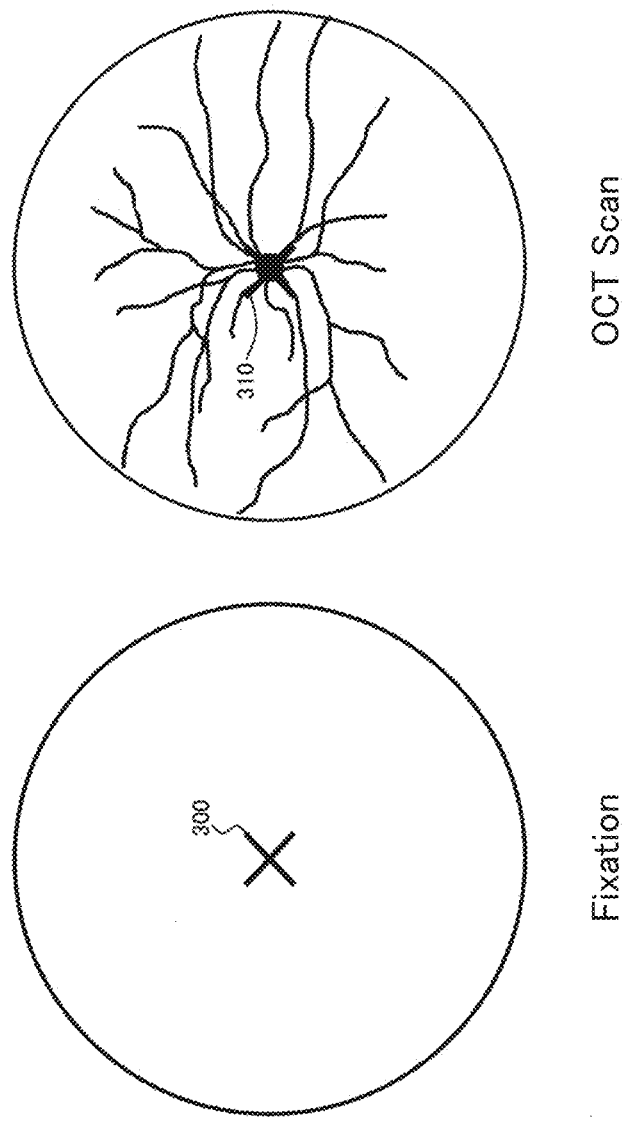

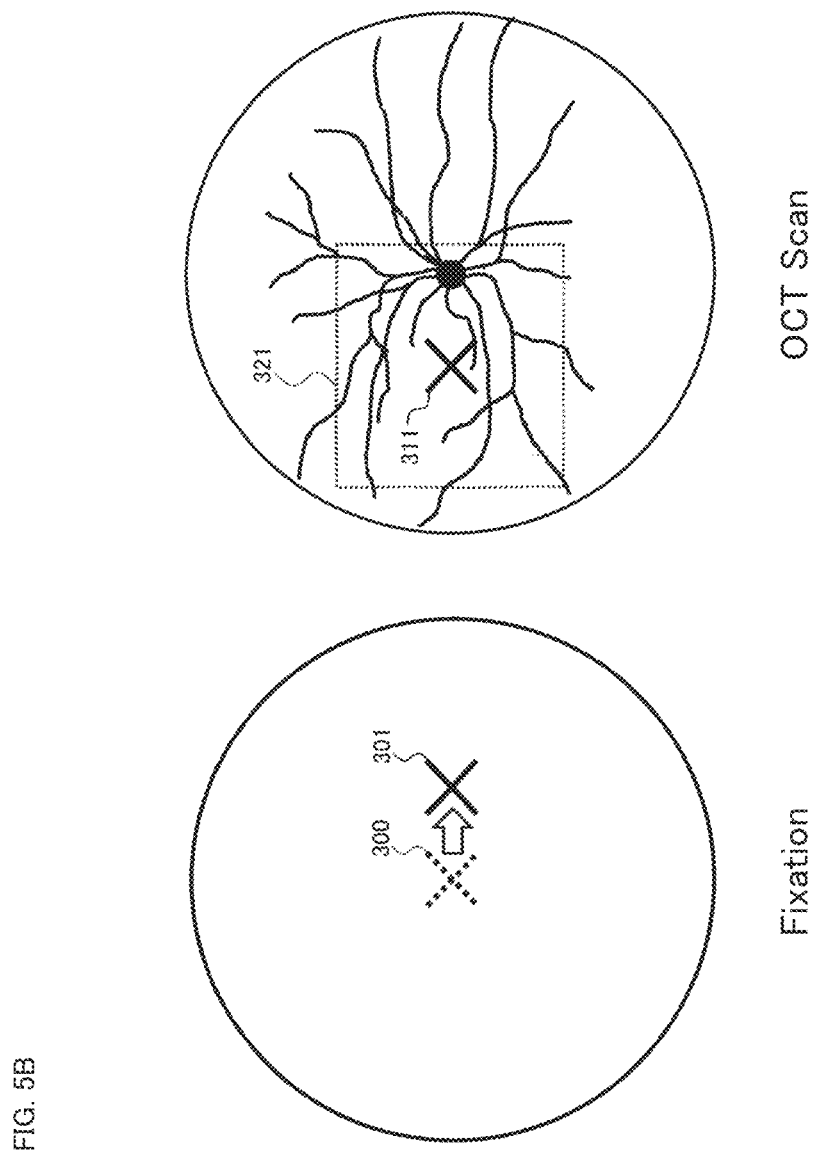

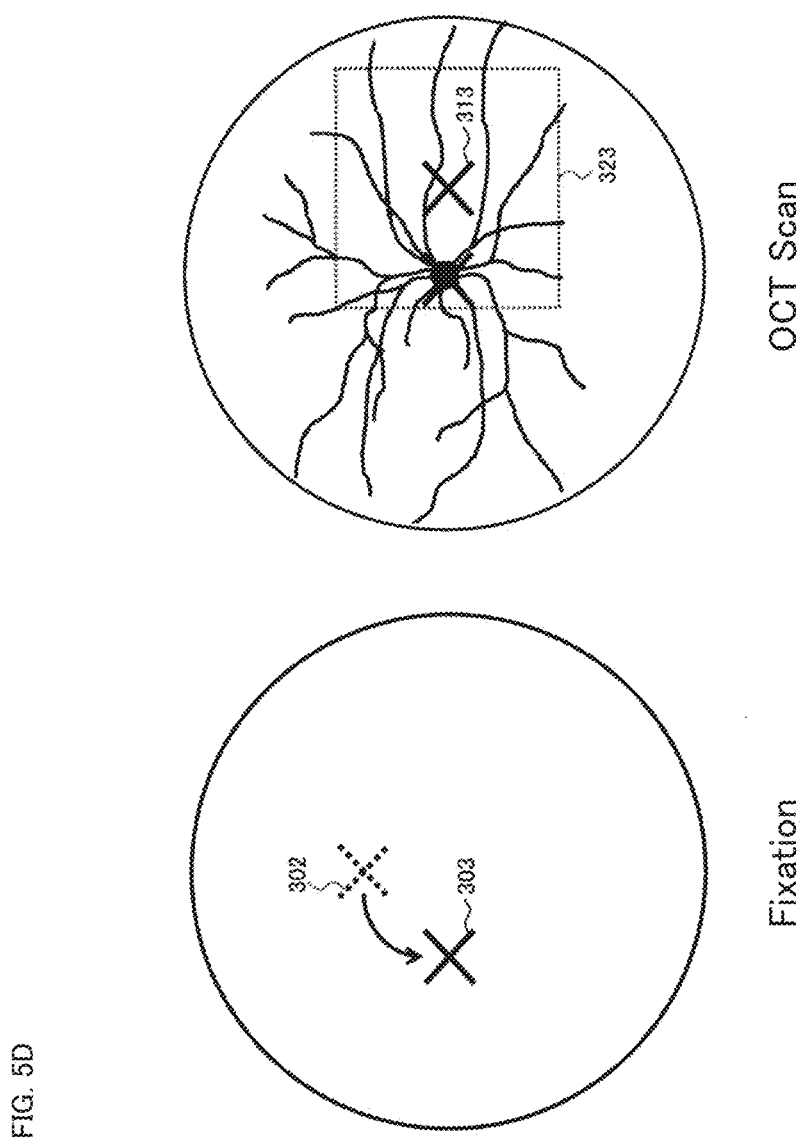

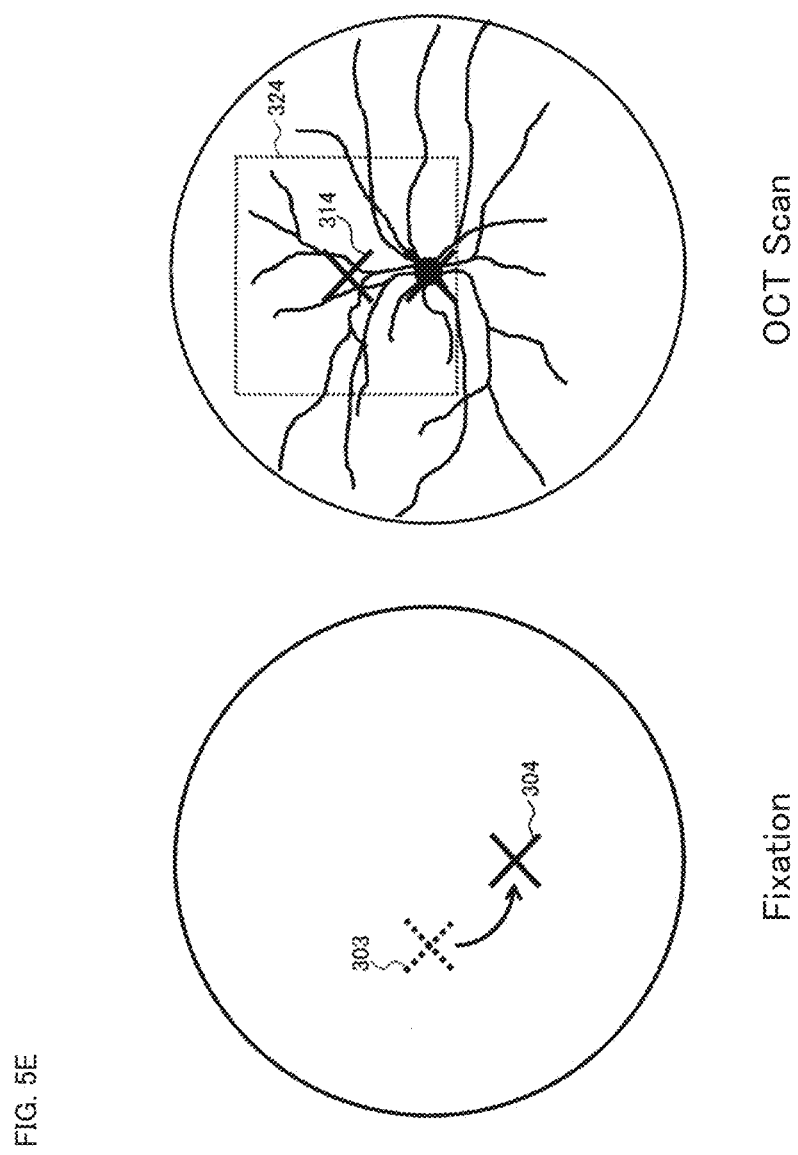

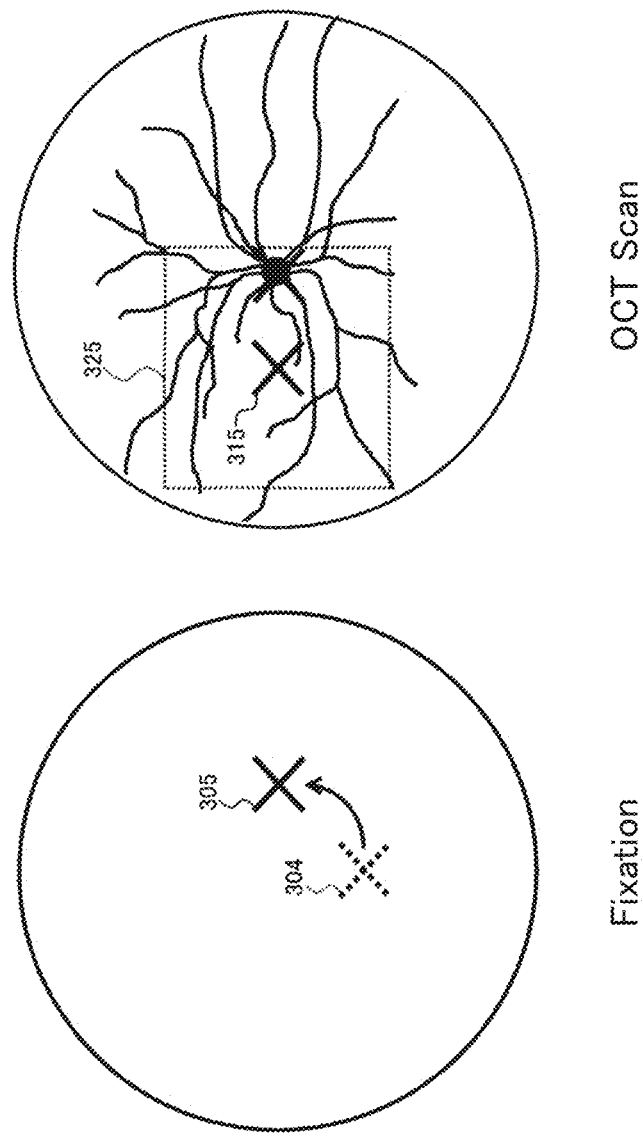

SCANNING IMAGING APPARATUS, METHOD OF CONTROLLING THE SAME, SCANNING IMAGING METHOD, AND RECORDING MEDIUM

CROSS-REFERENCE TO RELATED APPLICATION

This application is based upon and claims the benefit of priority from Japanese Patent Application No. 2019-164245, filed Sep. 10, 2019; the entire contents of which are incorporated herein by reference.

FIELD

The present disclosure relates to a scanning imaging apparatus, a method of controlling the same, a scanning imaging method, and a recording medium.

BACKGROUND

Scanning imaging is one of the imaging technologies. Scanning imaging is a technique of sequentially acquiring data from a plurality of parts or sites of a sample and constructing an image of the sample from the data acquired.

Optical coherence tomography (OCT) is known as a typical example of scanning imaging techniques using light. OCT is a technique capable of constructing an image of a light scattering medium at a resolution of a micrometer level or higher. OCT has been applied to medical imaging, non-destructive examination, and the like. OCT is a technique based on low coherence interferometry, and typically utilizes near-infrared light to improve the reaching depth of light into a sample of a light scattering medium.

For example, OCT apparatuses have been widely used in ophthalmic diagnostic imaging. In ophthalmic diagnostic imaging, not only two-dimensional imaging but also three-dimensional imaging, structural analysis, functional analysis, etc. have been put to practical use as a powerful diagnostic tool. Furthermore, scanning imaging other than OCT, such as scanning laser ophthalmoscope (SLO), is also utilized in the field of ophthalmology. In addition, scanning imaging techniques that use ultrasonic waves or light (electromagnetic waves) in a wavelength band other than near-infrared light is also known.

From among various types of scanning mode used in OCT and SLO, "Lissajous scan", which is employed for the purpose of motion artifact correction or the like, has been drawing attention of late (for example, see Patent Documents 1 to 4 and Non-Patent Documents 1 and 2 below). A typical Lissajous scan performs high-speed scanning of measurement light along a loop (cycle) of a certain size. This makes it possible to substantially ignore the data acquisition time difference between the cycles and to perform position matching between the cycles by referring to the regions in which different cycles cross each other. Therefore, artifacts caused by the movement of the sample can be corrected. Focusing on this point, efforts are made in the field of ophthalmology to deal with artifacts caused by the involuntary eye movement.

In addition, enlargement of a scan area (that is, widening of the angle of view) is also making progress in the field of scanning imaging. For example, apparatuses have been developed in order to scan a wide area from the center to the periphery of an eye fundus by increasing the deflection angle of the optical scanner (e.g., galvanometer mirror, MEMS scanner, resonant scanner) and by optimizing the structure, control, and imaging processing in accordance with the increase of the deflection angle (for example, see Patent Documents 5 and 6 below).

Considering the technological progress as described above, combining Lissajous scan and widening of the angle of view comes to mind; however, the following problem is expected to arise. That is, if the path length of a cycle of the Lissajous scan is increased to widen the angle of view, the time required for scanning the cycle becomes longer. This leads to the difference between the data acquisition times from different points on the cycle becoming too large to ignore. As a result of this, the effectiveness of the motion artifact correction may be impaired. Widening the angle of view generally increases the time required to execute scanning. This in turn increases the influence of sample movement or sample motion and therefore increases the importance of the motion artifact correction. Considering these circumstances, it can be said that addressing this problem is one of the necessary conditions for practical application.

Patent Document 1: Japanese Unexamined Patent Application Publication No. 2016-017915
Patent Document 2: Japanese Unexamined Patent Application Publication No. 2018-068578
Patent Document 3: Japanese Unexamined Patent Application Publication No. 2018-140004
Patent Document 4: Japanese Unexamined Patent Application Publication No. 2018-140049
Patent Document 5: Japanese Unexamined Patent Application Publication No. 2017-086311
Patent Document 6: Japanese Unexamined Patent Application Publication No. 2017-047113
Non-Patent Document 1: Yiwei Chen, Young-Joo Hong, Shuichi Makita, and Yoshiaki Yasuno, "Three-dimensional eye motion correction by Lissajous scan optical coherence tomography", Biomedical Optics EXPRESS, Vol. 8, No. 3, 1 Mar. 2017, PP. 1783-1802.
Non-Patent Document 2: Yiwei Chen, Young-Joo Hong, Shuichi Makita, and Yoshiaki Yasuno, "Eye-motion-corrected optical coherence tomography angiography using Lissajous scanning", Biomedical Optics EXPRESS, Vol. 9, No. 3, 1 Mar. 2018, PP. 1111-1129.

SUMMARY

One object of aspect examples according to the present disclosure is to achieve an appropriate integration of Lissajous scan and widening of the angle of view.

Some aspect examples relate to a scanning imaging apparatus. The scanning imaging apparatus includes a scanner, a scan controller, a movement unit, a movement controller, and an image constructing unit. The scanner is configured to apply an optical scan to a sample to acquire data. The scan controller is configured to perform control of the scanner to sequentially apply a plurality of pattern scans according to a predetermined two-dimensional pattern including a series of cycles to the sample. The movement unit is configured to relatively move a scan area corresponding to the two-dimensional pattern and the sample. The movement controller is configured to perform control of the movement unit such that a cycle in a first scan of the plurality of pattern scans and a cycle in a second scan cross each other at least at one point. The image constructing unit is configured to construct an image based on data acquired by the scanner under the control performed by the scan controller and the control performed by the movement controller. The scan controller and the movement controller perform the control of the scanner and the control of the movement unit respectively such that, for each of the plurality of pattern scans, a first cycle and a second cycle in a pattern scan cross each other at least at one point.

In some aspect examples, the scanner includes a first deflector configured to deflect light in a first direction and a second direction that are mutually different. In addition, the scan controller sequentially applies the plurality of pattern scans to the sample by performing control of the first deflector such that a deflection direction change along the first direction is iterated with a first period while a deflection direction change along the second direction is iterated with a second period different from the first period.

In some aspect examples, the sample is a living eye. In addition, the movement unit includes a fixation light projector configured to project fixation light onto the living eye. Further, the movement controller performs control of the fixation light projector to change a projection direction of the fixation light with respect to the living eye.

In some aspect examples, the movement unit includes a second deflector configured to deflect light guided by the scanner. In addition, the movement controller performs control of the second deflector to change a deflection direction of the light guided by the scanner.

In some aspect examples, the movement unit includes a movement mechanism configured to move at least part of at least the scanner. In addition, the movement controller performs control of the movement mechanism to move the at least part of at least the scanner with respect to the sample.

In some aspect examples, the movement controller performs the control of the movement unit to relatively move the scan area and the sample along a predetermined path.

In some aspect examples, the predetermined path is a closed path.

In some aspect examples, the predetermined path is a circular path.

In some aspect examples, the movement controller performs the control of the movement unit to relatively move the scan area and the sample in a continuous or stepwise manner.

In some aspect examples, the movement controller performs the control of the movement unit such that the cycle in the first scan and the cycle in the second scan cross each other at least at two points.

In some aspect examples, the movement controller performs the control of the movement unit such that the cycle in the first scan and the cycle in the second scan cross each other at least at four points.

In some aspect examples, the scan controller and the movement controller perform the control of the scanner and the control of the movement unit respectively such that the first cycle and the second cycle cross each other at least at two points.

In some aspect examples, the scan controller performs the control of the scanner based on a scan protocol generated based on a Lissajous function in advance.

Some aspect examples relate to a method of controlling a scanning imaging apparatus. The scanning imaging apparatus includes a scanner, a movement unit, and an image constructing unit. The scanner is configured to apply an optical scan to a sample to acquire data. The movement unit is configured to relatively move the sample and an area to which the optical scan is applied. The image constructing unit is configured to construct an image based on the data acquired by the scanner. The method includes the following steps: performing control of the scanner to sequentially apply a plurality of pattern scans according to a predetermined two-dimensional pattern including a series of cycles to the sample; performing control of the movement unit such that a cycle in a first scan of the plurality of pattern scans and a cycle in a second scan cross each other at least at one point; performing control of the scanner and control of the movement unit in such a manner that, for each of the plurality of pattern scans, a first cycle and a second cycle in a pattern scan cross each other at least at one point; and constructing an image based on data acquired by the scanner during the control of the scanner and the control of the movement unit.

Some aspect examples relate to a program configured to cause a computer to execute the method of controlling the scanning imaging apparatus.

Some aspect examples relate to a computer-readable non-transitory recording medium that stores a program configured to cause a computer to execute the method of controlling the scanning imaging apparatus.

Some aspect examples relate to an imaging method of constructing an image based on data acquired by applying an optical scan to a sample. The method includes the following steps: sequentially applying a plurality of pattern scans according to a predetermined two-dimensional pattern including a series of cycles to the sample; relatively moving the sample and an area to which the optical scan is applied such that a cycle in a first scan of the plurality of pattern scans and a cycle in a second scan cross each other at least at one point; performing sequential application of the plurality of pattern scans and relative movement between the area and the sample in such a manner that, for each of the plurality of pattern scans, a first cycle and a second cycle in a pattern scan cross each other at least at one point; acquiring data by applying an optical scan to the sample in parallel with the sequential application of the plurality of pattern scans and the relative movement between the area and the sample; and constructing an image based on the data acquired.

Some aspect examples relate to a program configured to cause a computer to execute the imaging method.

Some aspect examples relate to a computer-readable non-transitory recording medium that stores a program configured to cause a computer to execute the imaging method.

BRIEF DESCRIPTION OF THE DRAWINGS

FIG. 5A is a schematic diagram for describing an example of an OCT scan executed by the scanning imaging apparatus (ophthalmic apparatus) according to the embodiment example.

FIG. 5B is a schematic diagram for describing an example of an OCT scan executed by the scanning imaging apparatus (ophthalmic apparatus) according to the embodiment example.

FIG. 5D is a schematic diagram for describing an example of an OCT scan executed by the scanning imaging apparatus (ophthalmic apparatus) according to the embodiment example.

FIG. 5E is a schematic diagram for describing an example of an OCT scan executed by the scanning imaging apparatus (ophthalmic apparatus) according to the embodiment example.

FIG. 5F is a schematic diagram for describing an example of an OCT scan executed by the scanning imaging apparatus (ophthalmic apparatus) according to the embodiment example.

DETAILED DESCRIPTION

Some embodiment examples relating to a scanning imaging apparatus, a method of controlling the same, a scanning imaging method, a program, and a recording medium will be described in detail with reference to the drawings. Any of the technologies or techniques disclosed in the documents cited in the present specification and any other known technologies or techniques may be applied to or combined with the embodiment examples. Further, "image data" and an "image" formed based thereon are not distinguished unless otherwise mentioned. Furthermore, a "site" of the subject's eye and an "image" thereof are not distinguished unless otherwise mentioned.

The scanning imaging apparatus according to the embodiment examples described below is an ophthalmic apparatus capable of measuring the fundus of a living eye using Fourier domain OCT such as swept source OCT. The types of OCT techniques applicable to embodiments are not limited to swept source OCT. Spectral domain OCT or time domain OCT may also be applied, for example.

The ophthalmic apparatus according to the embodiment examples may be capable of processing not only data acquired by using OCT but also data acquired by using other modalities. The other modalities may be any of a fundus camera, a scanning laser ophthalmoscope (SLO), a slit lamp microscope, and an ophthalmic surgical microscope, for example. The ophthalmic apparatus according to the embodiment examples may have the function of any of such modalities.

The target (sample) to which OCT is applied is not limited to the fundus of an eye. The target (sample) may be any site of an eye such as the anterior segment or the vitreous body. Furthermore, the target (sample) may be a site or tissue of a living body other than an eye, or may also be an object other than a living body.

<Configuration>

Figure 1:
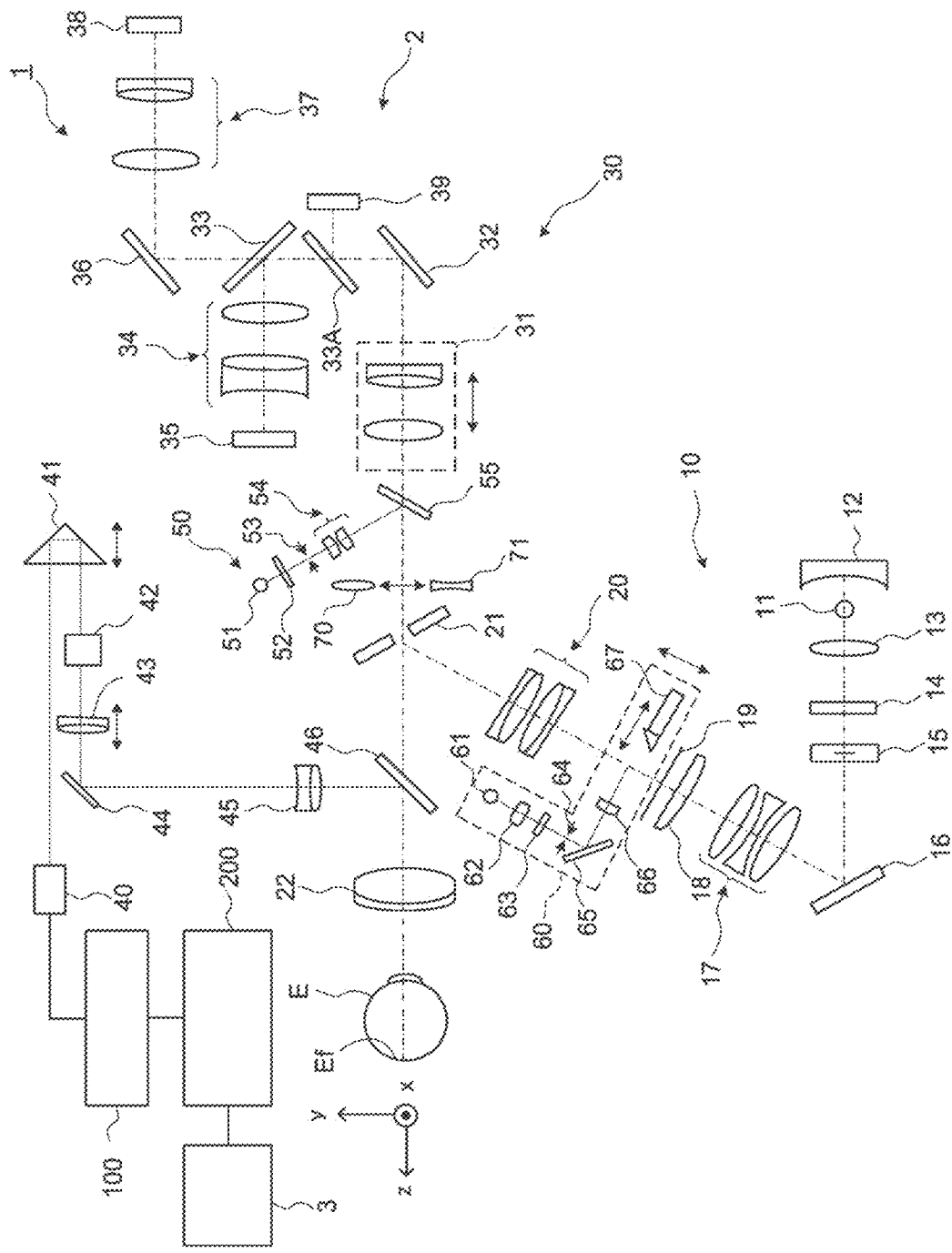
FIG. 1 is a schematic diagram showing an example of the configuration of the scanning imaging apparatus (ophthalmic apparatus) according to the embodiment example.

The ophthalmic apparatus 1 shown in FIG. 1 is one aspect example of a scanning imaging apparatus. The ophthalmic apparatus 1 includes the fundus camera unit 2, the OCT unit 100 and the arithmetic and control unit 200. The fundus camera unit 2 is provided with an element group (e.g., optical elements, mechanisms, etc.) for photographing the subject's eye E from the front. The OCT unit 100 includes part of an element group (e.g., optical elements, mechanisms, etc.) for applying OCT scans to the subject's eye E. Another part of the element group for OCT scanning is provided in the fundus camera unit 2. The arithmetic and control unit 200 includes one or more processors configured and programmed to execute various calculations and controls. In addition to these, the ophthalmic apparatus 1 may also include elements for supporting the face of the subject and an element for switching the site to which OCT scanning is applied. Examples of the elements for supporting the face of the subject include a chin rest and a forehead rest. Examples of the element for switching the sites to which OCT scanning is applied include a lens unit used to switch the target site from the fundus to the anterior segment.

In the present specification, the "processor" may have any circuit configuration. For example, the processor includes a circuit such as a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), or the like. The processor executes a program stored in a memory circuit or a storage device to implement below-mentioned functions according to the embodiment.

<Fundus Camera Unit 2>

The fundus camera unit 2 is provided with an optical system for photographing the fundus Ef of the subject's eye E. Images of the fundus Ef acquired by the fundus camera unit 2 (referred to as fundus images, fundus photographs, or the like) are front images such as observation images and photographed images. An observation image is obtained, for example, by capturing a moving image using near-infrared light, and is used for alignment, focusing, tracking, and the like. A photographed image is a still image obtained by using flash light in the visible or infrared bands, for example.

The fundus camera unit 2 includes the illumination optical system 10 and the photographing optical system 30. The illumination optical system 10 projects illumination light onto the subject's eye E. The photographing optical system 30 detects return light of the illumination light from the subject's eye E. Measurement light guided from the OCT unit 100 is directed to the subject's eye E through the optical path in the fundus camera unit 2, and return light of the measurement light from the subject's eye E is directed to the OCT unit 100 through the same optical path.

Light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the area surrounding the aperture part) of the aperture mirror 21, penetrates the dichroic mirror 46, and is refracted by the objective lens 22, thereby illuminating the subject's eye E (the fundus Ef). Return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light passes through the half mirror 33A, is reflected by the dichroic mirror 33, and forms an image on the light receiving surface of the image sensor 35 by the imaging lens 34. The image sensor 35 detects the return light at a predetermined frame rate. Note that the photographing optical system 30 is focused on the fundus Ef or the anterior eye segment.

Light output from the photographing light source 15 (referred to as photographing illumination light) passes through the same route as that of the observation illumination light and is projected onto the fundus Ef. Return light of the photographing illumination light from the subject's eye E passes through the same route as that of the return light of the observation illumination light up to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (fixation target image). Part of a light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef. Varying the display position of the fixation target image on the LCD 39 changes the direction in which the line of sight of the subject's eye E is guided (fixation direction, fixation position).

For example, a light emitting element array or a combination of a light emitting element and a mechanism for moving the light emitting element may be used in place of a display device such as the LCD 39.

The alignment optical system 50 generates an alignment indicator used for the alignment of the optical system with respect to the subject's eye E. Alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. Return light of the alignment light from the subject's eye E (e.g., the corneal reflection light) passes through the same route as that of the return light of the observation illumination light and is guided to the image sensor 35. The manual alignment and/or the automatic alignment may be carried out on the basis of an image detected by the image sensor 35 (alignment indicator image).

As in conventional cases, the alignment indicator image of the present example includes two bright spot images whose positions change depending on alignment states. When the relative position between the subject's eye E and the optical system changes in the xy direction, the two bright spot images are shifted together in the xy direction. When the relative position between the subject's eye E and the optical system changes in the z direction, the relative position (distance) between the two bright spot images changes. When the distance between the subject's eye E and the optical system in the z direction matches with a working distance set in advance, the two bright spot images overlap with each other. When the position of the subject's eye E matches with the position of the optical system in the xy direction, the two bright spot images are located within or near a given alignment target. When the distance between the subject's eye E and the optical system in the z direction matches with the working distance as well as the position of the subject's eye E matches with the position of the optical system in the xy direction, the two bright spot images overlap with each other and are presented within the alignment target.

For the automatic alignment, the data processor 230 detects the positions of the two bright spot images, and the main controller 211 controls the movement mechanism 150 (described later) on the basis of the positional relationship between the two bright spot images and the alignment target. For the manual alignment, the main controller 211 displays the two bright spot images together with the observation image of the subject's eye E on the display 241, and the user operates the movement mechanism 150 using the operation device 242 while referring to the two bright spot images displayed.

The focus optical system 60 generates a split indicator used for the focus adjustment with respect to the subject's eye E. The focus optical system 60 is moved along the optical path of the illumination optical system 10 in conjunction with the movement of the photography focusing lens 31 along the optical path of the photographing optical system 30. The optical path of the illumination optical system 10 is referred to as the illumination optical path, and the optical path of the photographing optical system 30 is referred to as the photographing optical path. The reflection rod 67 is inserted into and removed from the illumination optical path. The reflective surface of the reflection rod 67 is inserted into the illumination optical path and placed in a slanted position before performing focus adjustment. Focus light emitted from the LED 61 passes through the relay lens 62, is split into two light beams by the split indicator plate 63, and passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. Return light of the focus light from the subject's eye E (fundus reflection light etc.) passes through the same route as that of the return light of the alignment light and is guided to the image sensor 35. The manual focusing and/or the automatic focusing may be carried out on the basis of an image detected by the image sensor 35 (split indicator image).

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT scanning (measurement arm). The dichroic mirror 46 reflects the light of wavelength bands used for OCT scanning and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrow in FIG. 1, whereby the length of the measurement arm is changed. Changing the measurement arm length may be utilized for optical path length correction according to axial length and for adjustment of interference conditions and states.

The dispersion compensation member 42, together with the dispersion compensation member 113 (described later) arranged in the reference arm, acts to equalize the dispersion characteristics of the measurement light LS and the dispersion characteristics of the reference light LR with each other.

The OCT focusing lens 43 is moved along the measurement arm in order to perform the focus adjustment of the measurement arm. The movement of the photography focusing lens 31, the movement of the focus optical system 60, and the movement of the OCT focusing lens 43 may be controlled in an interlocking manner.

The optical scanner 44 is placed substantially at a position optically conjugate with the pupil of the subject's eye E. The optical scanner 44 deflects the measurement light LS guided through the measurement arm. The optical scanner 44 is, for example, a galvanometer scanner that is capable of two-dimensional scanning and includes a galvanometer mirror for performing scanning in the x direction and a galvanometer mirror for performing scanning in the y direction.

<OCT Unit 100>

Figure 2:
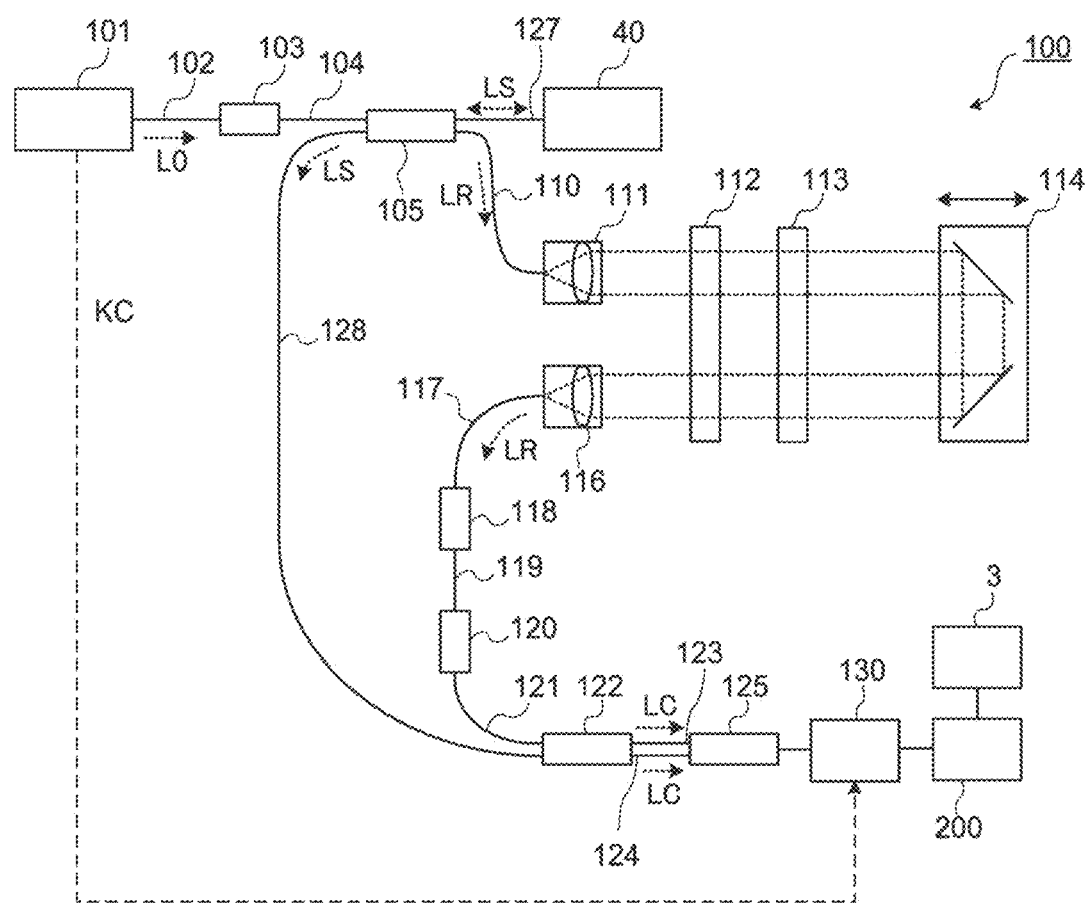
FIG. 2 is a schematic diagram showing an example of the configuration of the scanning imaging apparatus (ophthalmic apparatus) according to the embodiment example.

As illustrated in FIG. 2, the OCT unit 100 is provided with an optical system for applying swept source OCT. The optical system includes an interference optical system. The interference optical system is configured to split light emitted from a light source of wavelength tunable type (or, of wavelength sweeping type) into measurement light and reference light, superpose return light of the measurement light from the subject's eye E with the reference light having traveled along the reference optical path to generate interference light, and detect the interference light. Data (detection signal) obtained by the interference optical system is a signal representing a spectrum of the interference light, and is sent to the arithmetic and control unit 200.

The light source unit 101 includes, for example, a near-infrared tunable laser configured to vary the wavelengths of emitted light at high speed at least over near-infrared wavelength bands. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR. The optical path of the measurement light LS is referred to as a measurement arm or a sample arm, and the optical path of the reference light LR is referred to as a reference arm.

The reference light LR is guided through the optical fiber 110 to the collimator 111, is converted into a parallel light beam by the collimator 111, travels through the optical path length correction member 112 and the dispersion compensation member 113, and is guided to the retroreflector 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 provided in the measurement arm. The retroreflector 114 is movable along the optical path of the reference light LR being incident on the retroreflector 114. With this, the length of the reference arm is changed. Changing the length of the reference arm may be utilized for optical path length correction according to axial length and for adjustment of interference conditions and states.

The reference light LR that has passed through the retroreflector 114 travels through the dispersion compensation member 113 and the optical path length correction member 112, is converted from a parallel light beam to a convergent light beam by the collimator 116, and is incident on the optical fiber 117. The reference light LR having been incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. Return light of the measurement light LS from the subject's eye E travels along the same route as the outward way in the opposite direction up to the fiber coupler 105, and then reaches the fiber coupler 122 via the optical fiber 128.

The fiber coupler 122 superposes the measurement light LS guided by the optical fiber 128 with the reference light LR guided by the optical fiber 121 to generate interference light. The fiber coupler 122 splits the generated interference light at a predetermined splitting ratio (e.g., 1 to 1) to generate a pair of interference light LC. The pair of the interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs a difference signal between a pair of detection signals corresponding to the pair of the interference light LC respectively obtained by the pair of photodetectors. The detector 125 sends the output (difference signal) to the data acquisition system (DAS) 130.

The clock KC is supplied from the light source unit 101 to the data acquisition system 130. The clock KC is generated in the light source unit 101 in synchronization with the output timings of wavelengths varied over a predetermined wavelength range by the wavelength tunable type light source. For example, the light source unit 101 is configured to split the light L0 of each output wavelength to generate two pieces of split light, apply an optical delay to one of the two pieces of split light, combine the resulting two pieces of split light, detect the combined light, and generate the clock KC based on the detection result of the combined light. The data acquisition system 130 performs sampling of the detection signal input from the detector 125 based on the clock KC. The data acquisition system 130 sends the result of the sampling to the arithmetic and control unit 200.

The present example is provided with both an element for changing the measurement arm length (e.g., the retroreflector 41) and an element for changing the reference arm length (e.g., the retroreflector 114 or a reference mirror). However, some other embodiments may include only either one of these elements. An element for changing the difference between the measurement arm length and the reference arm length (i.e., an element for changing the optical path length difference) is not limited to the elements described above, and may be any type of element such as any type of optical members and any type of mechanisms.

<Control System and Processing System>

Figure 3:
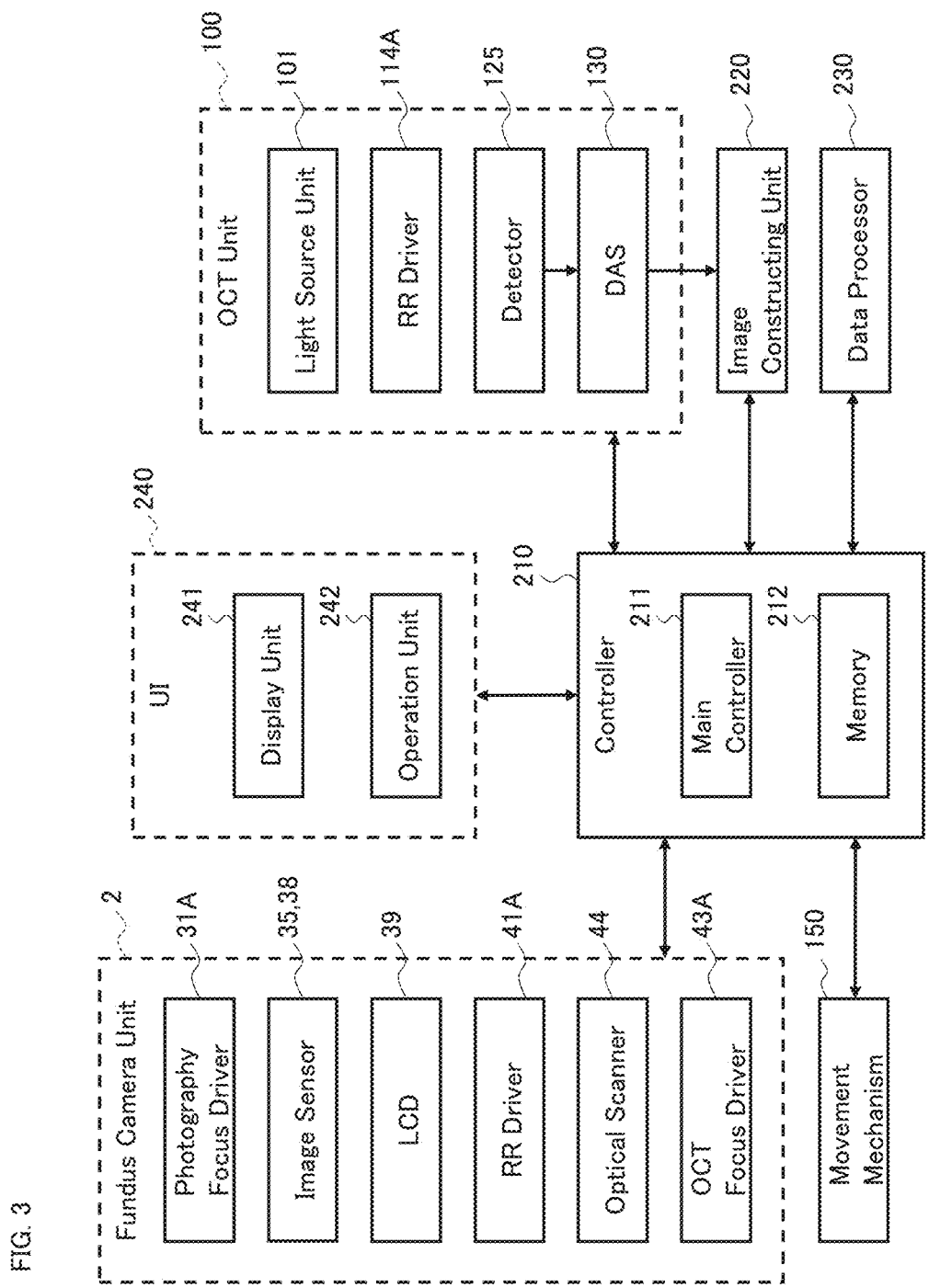
FIG. 3 is a schematic diagram showing an example of the configuration of the scanning imaging apparatus (ophthalmic apparatus) according to the embodiment example.
Figure 4:
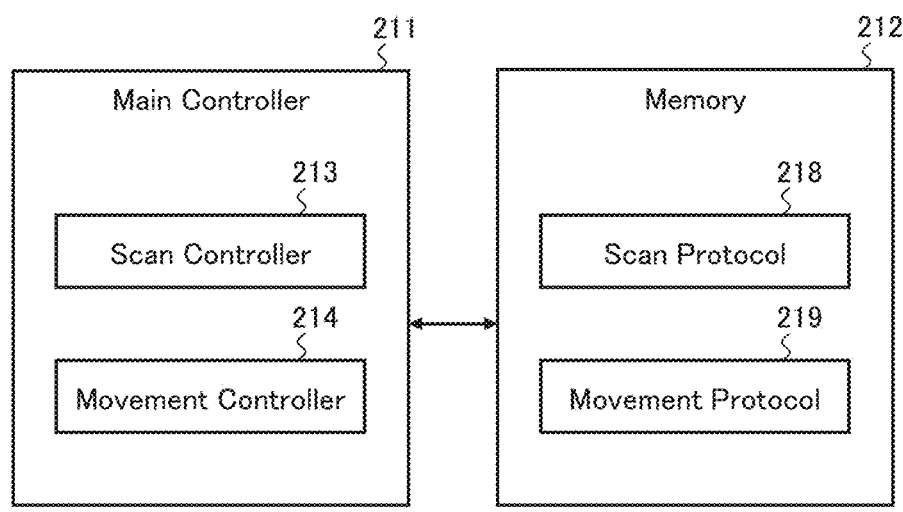
FIG. 4 is a schematic diagram showing an example of the configuration of the scanning imaging apparatus (ophthalmic apparatus) according to the embodiment example.

FIG. 3 and FIG. 4 show an example of the configuration of the control system and the processing system of the ophthalmic apparatus 1. The controller 210, the image constructing unit 220, and the data processor 230 are provided in the arithmetic and control unit 200, for example. The ophthalmic apparatus 1 may include a communication device for performing data communication with an external apparatus. The ophthalmic apparatus 1 may include a drive device (reader and/or writer) for reading out data from a recording medium and/or writing data into a recording medium.

<Controller 210>

The controller 210 performs various kinds of controls. The controller 210 includes the main controller 211 and the memory 212. Further, as shown in FIG. 4, the controller 210 includes the scan controller 213 and the movement controller 214, and the memory 212 stores the scan protocol 218 and the movement protocol 219 in the present embodiment.

<Main Controller 211>

The main controller 211 includes a processor(s) and controls each unit and each element of the ophthalmic apparatus 1 (including the units and elements shown in FIG. 1 to FIG. 4). The main controller 211 is implemented by cooperation between hardware including the processor(s) and control software.

The main controller 211 may operate the scan controller 213 and the movement controller 214 in an interlocking manner (i.e., in a synchronous manner). The scan controller 213 performs OCT scan control regarding a scan area having a predetermined shape and a predetermined size. The movement controller 214 performs control for relatively moving the scan area and the sample (the subject's eye E). The interlocking operation (or, synchronous operation or cooperation) of the scan control and the movement control makes it possible for an OCT scan to be applied to an area having a size larger than the scan area. In other words, the interlocking operation makes it possible for an OCT scan to be applied to a wide area. Such an OCT scan is referred to as a wide area scan.

The photography focus driver 31A moves the photography focusing lens 31 disposed in the photographing optical path and the focus optical system 60 disposed in the illumination optical path under control of the main controller 211. The retroreflector driver (RR driver) 41A moves the retroreflector 41 disposed in the measurement arm under control of the main controller 211. The OCT focus driver 43A moves the OCT focusing lens 43 disposed in the measurement arm under control of the main controller 211. The optical scanner 44 disposed in the measurement arm operates under control of the main controller 211 (under control of the scan controller 213). The retroreflector driver (RR driver) 114A moves the retroreflector 114 disposed in the reference arm under control of the main controller 211. Each of the drivers described above includes an actuator such as a pulse motor that operates in response to control of the main controller 211.

The movement mechanism 150 typically moves the fundus camera unit 2 in a three-dimensional manner. The movement mechanism 150 includes, for example, the following elements: an x stage that can be moved in the ±x direction (i.e., left and right direction); an x movement mechanism that moves the x stage; a y stage that can be moved in the ±y direction (i.e., up and down direction); a y movement mechanism that moves the y stage; a z stage that can be moved in the ±z direction (i.e., depth direction); and a z movement mechanism that moves the z stage. Each of the aforesaid movement mechanisms includes an actuator such as a pulse motor that operates in response to control of the main controller 211.

<Memory 212>

The memory 212 stores various kinds of data. Examples of data stored in the memory 212 include OCT images, fundus images, subject's eye information, and control information. The subject's eye information includes subject information such as a patient ID and a patient's name, identification information for right and left eyes, and electronic medical record information. The control information is information regarding specific control. The control information in the present embodiment includes the scan protocol 218 and the movement protocol 219.

The scan protocol 218 is a defined set of rules or regulations regarding the contents of control for application of OCT scanning to a scan area having a predetermined shape and a predetermined size. The scan protocol 218 includes a set of various kinds of control parameters (scan control parameters). The scan protocol 218 includes a protocol for each scan mode. The scan protocol 218 of the present embodiment includes at least a protocol for a Lissajous scan, and may further include protocols for other scan modes such as a protocol for a B-scan (line scan), a protocol for a cross scan, a protocol for a radial scan, and a protocol for a raster scan.

The scan control parameters of the present embodiment include at least a parameter indicating a content of control for the optical scanner 44. Examples of such parameters include a parameter indicating a scan pattern, a parameter indicating a scan speed, and a parameter indicating a scan interval. A scan pattern indicates the shape of a scan path, and examples thereof include a Lissajous pattern, a line pattern, a cross pattern, a radial pattern, and a raster pattern. A scan speed is defined, for example, as a repetition rate of A-scans. A scan interval is defined, for example, as an interval (or a distance) between adjacent A-scans, that is, as array intervals (arrangement intervals, disposition intervals) of scan points.

It should be noted that, as in the conventional technologies and techniques as disclosed in Patent Documents 1 to 4 and Non-Patent Documents 1 and 2 mentioned above, a "Lissajous scan" of the present embodiment may not only be a Lissajous scan in a "narrow sense" whose path is a pattern drawn by a locus of points represented and obtained as an ordered pair of two simple harmonic motion orthogonal to each other (referred to as a Lissajous pattern, a Lissajous figure, a Lissajous curve, a Lissajous function, or a Bowditch curve), but also may be a Lissajous scan in a "broad sense" obtained from a predetermined two-dimensional pattern that includes a series of cycles.

The optical scanner 44 of the present embodiment includes a first galvanometer mirror and a second galvanometer mirror. The first galvanometer mirror deflects the measurement light LS in the x direction and the second galvanometer mirror deflects the measurement light LS in the y direction. A Lissajous scan is implemented by simultaneously performing the following two controls: control of the first galvanometer mirror to iterate the change in the deflection direction along the x direction with the first period; and control of the second galvanometer mirror to iterate the change in the deflection direction along the y direction with the second period. Here, the first period and the second period are different from each other.

For example, a Lissajous scan of the present embodiment is not limited to a scan of a Lissajous pattern in the narrow sense obtained from the combination of two sine waves; however, a Lissajous scan of the present embodiment may also be a scan of a pattern generated by adding a specific term (e.g., a polynomial of an odd order) to a Lissajous pattern in the narrow sense, or a scan of a pattern based on a triangular wave.

A "cycle" generally means an object composed of a plurality of sampling points and having a certain length, and may be a closed curve or a nearly closed curve, for example.

Typically, the scan protocol 218 is generated based on a Lissajous function. Note that a Lissajous function is expressed, for example, by the following parametric equation system: $x(t_i)=A\cos(2\pi(f_A/n)t_i)$, $y(t_i)=A\cos(2\pi(f_A(n-2)/n^2)t_i)$.

Here, "x" denotes the horizontal axis of the two-dimensional coordinate system in which the Lissajous curve is defined and "y" denotes the vertical axis. Further, "$t_i$" denotes the acquisition time point of the i-th A-line in the Lissajous scan, "A" denotes the scan area (amplitude), "$f_A$" denotes the acquisition rate of the A-lines (i.e., A-scan speed, A-scan repetition rate), and "n" denotes the number of A-lines in each cycle in the x direction (i.e., horizontal axis direction).

The movement protocol 219 is used in combination with the scan protocol 218. The movement protocol 219 is a defined set of rules or regulations regarding the content of control for performing relative movement between the scan area and the sample (the subject's eye E), and includes a set of various kinds of control parameters (movement control parameters). The movement protocol 219 may include a protocol for each scan mode. The movement protocol 219 of the present embodiment includes at least a protocol corresponding to a Lissajous scan, and may further include a protocol corresponding to arbitrary kinds of scan modes such as a B-scan (line scan), a cross scan, a radial scan, and a raster scan.

The movement control parameters of the present embodiment may include, for example, any one or more of the following parameters: (1) a parameter indicating a content of control for the LCD 39 that displays a fixation target image for guiding the direction of the line of sight of the subject's eye E; (2) a parameter indicating a content of control for the optical scanner 44 that deflects the measurement light LS; (3) a parameter indicating a content of control for the movement mechanism 150 that moves the fundus camera unit 2.

Movement control parameters are not limited to those mentioned above. In general, a movement control parameter may be an arbitrary kind of parameter for defining a relative movement mode between the subject's eye E and a target area (a scan area having a predetermined shape and a predetermined size) of an OCT scan of a specific scan mode. Movement control parameters may include, for example, a parameter indicating a relative movement pattern, a parameter indicating a relative movement speed, and the like.

A relative movement pattern indicates the shape of a path of relative movement between a scan area and the subject's eye E. The relative movement pattern may be, for example, a continuous pattern and/or a discrete pattern. Examples of a continuous pattern include a circular pattern, an elliptic pattern, a square pattern, a rectangular pattern, a linear pattern, a curved line pattern, and the like. Examples of a discrete pattern include a point group pattern composed of a plurality of points in a particular disposition, a line group pattern composed of a plurality of line segments in a particular disposition, and a pattern formed of a combination of one or more point group patterns and one or more line group patterns. Moreover, one or more continuous patterns and one or more discrete patterns may be combined.

Thus, a relative movement between a scan area and the subject's eye E may be continuous or stepwise (intermittent). The start point and the end point of a relative movement pattern (relative movement path) may be the same or different. In other words, a relative movement pattern may form a closed path or an open path. Further, a relative movement pattern may be a path formed of a combination of one or more closed paths and one or more open paths.

If a relative movement pattern between a scan area and the subject's eye E is circular and if a Lissajous scan is performed (repeated) D times during this relative movement, the scan path formed of a combination of the D times of Lissajous scans and the relative movement is expressed, for example, as the following parametric equation system: $x(t_i)=A\cos(2\pi(f_A/n)t_i)+\cos((2\pi t_i/D))$, $y(t_i)=A\cos(2\pi(f_A(n-2)/n^2)t_i)-\sin((2\pi t_i/D))$.

The present embodiment may be configured to iterate a Lissajous scan a predetermined number of times based on the scan protocol 218 while performing a relative movement between the subject's eye E and a scan area of the Lissajous scan along a circular path based on the movement protocol 219.

In such a case, a plurality of Lissajous scans are sequentially executed and includes the first Lissajous scan and the second Lissajous scan. In addition, a cycle in the first Lissajous scan and a cycle in the second Lissajous scan cross each other at least at one point. Further, for each of the plurality of Lissajous scans sequentially executed, two cycles (the first cycle and the second cycle) in a Lissajous scan cross each other at least at one point.

Further, a plurality of Lissajous scans sequentially executed and a relative movement between a scan area and the subject's eye may be carried out in such a manner that a cycle in the first Lissajous scan and a cycle in the second Lissajous scan (among the plurality of Lissajous scans) cross each other at least at two points. In the present example, a cycle in the first Lissajous scan and a cycle in the second Lissajous scan intersect each other at least at four points.

In addition, for each of a plurality of Lissajous scans that are sequentially executed, two cycles (the first cycle and the second cycle) in a Lissajous scan cross each other at least at two points, in the present example.

As described above, the present example is configured to simultaneously execute the iteration (repetition) of Lissajous scans and the relative movement between the scan area and the subject's eye E in an interlocking manner, and also in such a manner that any pair of cycles in each Lissajous scan cross each other at one or more points (particularly at two or more points) and that a pair of cycles from any pair of Lissajous scans cross each other at one or more points (particularly at two or more points, and further, at four or more points). With such a configuration, position matching (alignment, registration) between a pair of data acquired from any pair of cycles in each Lissajous scan may be carried out, and position matching (alignment, registration) between a pair of data acquired from a pair of cycles in any pair of Lissajous scans. Therefore, position matching (alignment, registration) between all the cycles in the plurality of Lissajous scans sequentially executed becomes possible, and the image construction methods and techniques as well as the motion artifact correction methods and techniques, such as those disclosed in Non-Patent Document 1 or 2, can be applied to the present example.

Some examples of the interlocking operation of the scan control (control of Lissajous scan iteration) and the movement control (control of relative movement between the scan area and the subject's eye E) will be described. The present example executes iteration of Lissajous scans while continuously moving a scan area along a circular path. The movement control of the present example employs the movement control of the fixation target. The same may apply in the cases where other aspects of scan control and/or other aspects of movement control are employed.

To begin with, the present example presents a fixation target corresponding to a predetermined fixation position to the subject's eye E for alignment etc. The left figure in FIG. 5A shows the presentation position of the fixation target 300 corresponding to the optic nerve head, and the right figure shows the fundus Ef on which the fixation position of the left figure is presented. The reference character 310 in the right figure denotes the position of the fundus Ef corresponding to the presentation position of the fixation target 300.

After the completion of the alignment etc., the state where the fixation target 300 corresponding to the optic nerve head is presented is transferred to the state where the fixation target 301 is presented at a location on the right side of the optic nerve head, as shown in the left figure of FIG. 5B. The direction of the line of sight of the subject's eye E changes in response to the fixation position transition, and the scan area 321 is set as shown in the right figure of FIG. 5B. The scan area 321 is of a rectangular shape and its center is located at the position 311 that is shifted from the optic nerve head to the left. The outer edge (contour, outline) of the scan area 321 forms a circumscribed figure of a Lissajous scan pattern (the same applies to the following scan areas). Then, the present example starts OCT scanning (iterative Lissajous scan) from this state.

Figure 5C:
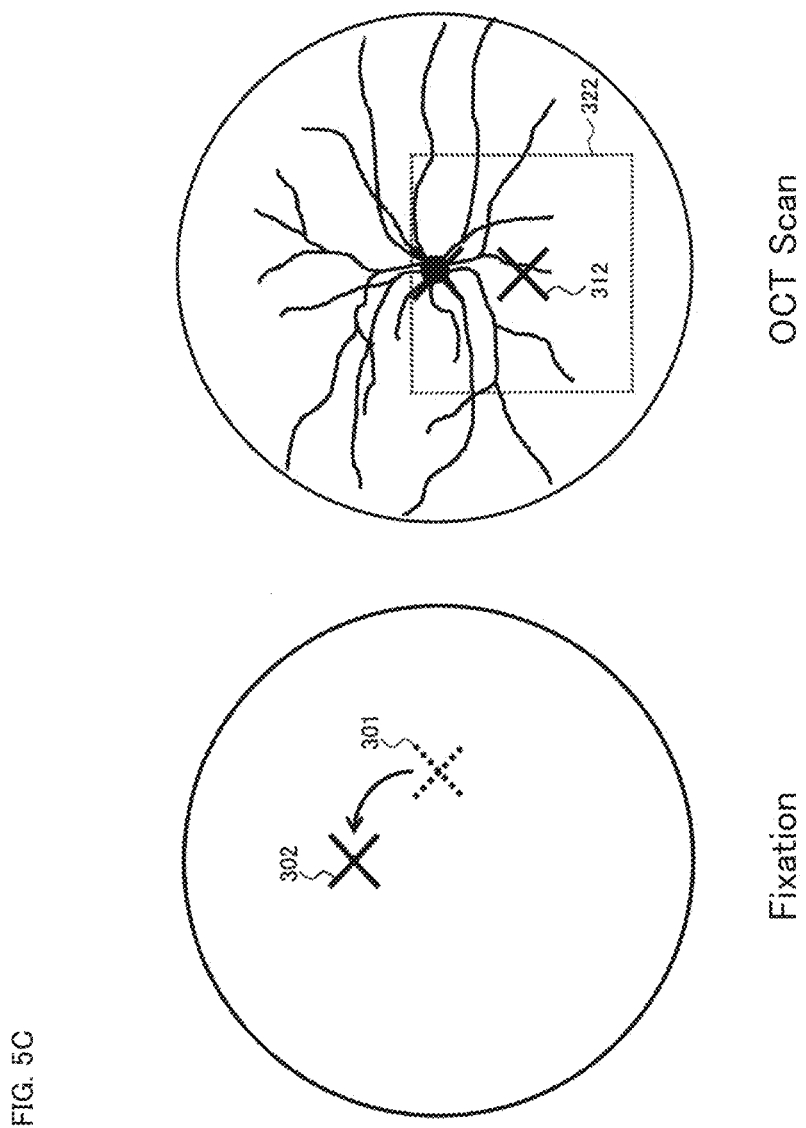
FIG. 5C is a schematic diagram for describing an example of an OCT scan executed by the scanning imaging apparatus (ophthalmic apparatus) according to the embodiment example.

The control of the relative movement between the scan area and the subject's eye E (movement control for the fixation position) is started together with the commencement of the control for OCT scanning (scan control). The present example continuously moves the fixation target along a circular path in the counterclockwise direction. The center of the circular path corresponds to the presentation position of the fixation target 300 shown in FIG. 5A. The radius of the circular path corresponds to the distance between the presentation position of the fixation target 300 and the presentation position of the fixation target 301. The left figure of FIG. 5C shows a further transition from the state in which the fixation target 301 is presented to the state in which the fixation target 302 is presented. The location of the fixation target 302 is shifted upward from the optic nerve head. This transition causes the direction of the line of sight of the subject's eye E to change. As a result of this, the scan area of the Lissajous scan continuously moves from the scan area 321 shown in the right figure of FIG. 5B to the rectangular scan area 322 shown in the right figure of FIG. 5C. Here, the center of the rectangular scan area 322 is located at the position 312 that is shifted downward from the optic nerve head.

Further, the left figure of FIG. 5D shows a transition from the state where the fixation target 302 is presented to the state where the fixation target 303 is presented. The fixation target 303 is located at a position shifted from the optic nerve head to the left. The direction of the line of the subject's eye E changes in response to the transition. As a result of this, the scan area of the Lissajous scan continuously moves from the scan area 322 shown in the right figure of FIG. 5C to the rectangular scan area 323 shown in the right figure of FIG. 5D. Here, the center of the rectangular scan area 323 is located at the position 313 shifted from the optic nerve head to the right.

Furthermore, the left figure of FIG. 5E shows a transition from the state where the fixation target 303 is presented to the state where the fixation target 304 is presented. The fixation target 304 is located below the optic nerve head. The direction of the line of sight of the subject's eye E changes in accordance with the transition. As a result of this, the scan area of the Lissajous scan continuously moves from the scan area 323 shown in the right figure of FIG. 5D to the rectangular scan area 324 shown in the right figure of FIG. 5E. Here, the center of the rectangular scan area 324 is located at the position 314 shifted upward from the optic nerve head.

In addition, the left figure of FIG. 5F shows a transition from the state where the fixation target 304 is presented to the state where the fixation target 305 is presented. The fixation target 305 is located at a position shifted from the optic nerve head to the right. The direction of the line of sight of the subject's eye E changes in accordance with the transition. As a result of this, the scan area of the Lissajous scan continuously moves from the scan area 324 shown in the right figure of FIG. 5E to the rectangular scan area 325 shown in the right figure of FIG. 5F. The center of the rectangular scan area 325 is located at the position 315 shifted from the optic nerve head to the left. Here, the presentation position of the fixation target 305 is the same as the presentation position of the fixation target 301 in FIG. 5B. The presentation position of the fixation target 305 is the end point of the OCT scan (the interlocking operation of the scan control and the movement control) of the present example, and the presentation position of the fixation target 301 is the starting point of the OCT scan of the present example.

Figure 6A:
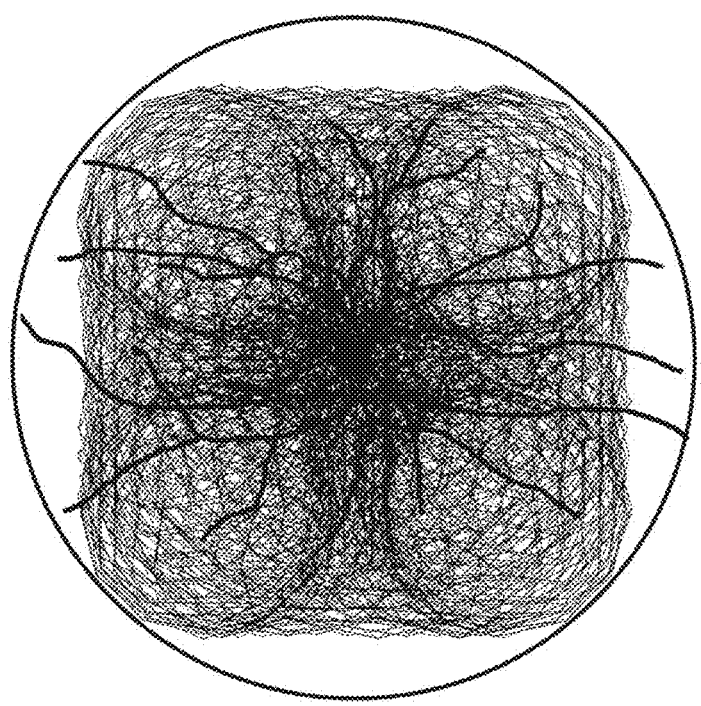
FIG. 6A is a schematic diagram for describing an example of an OCT scan executed by the scanning imaging apparatus (ophthalmic apparatus) according to the embodiment example.

FIG. 6A schematically shows the distribution of scan lines applied to the fundus Ef in the example shown in FIG. 5A to FIG. 5F. In other words, FIG. 6A schematically shows the distribution of the group of cycles of iterative Lissajous scan performed while continuously moving the scan area along the circular path.

Figure 6B:
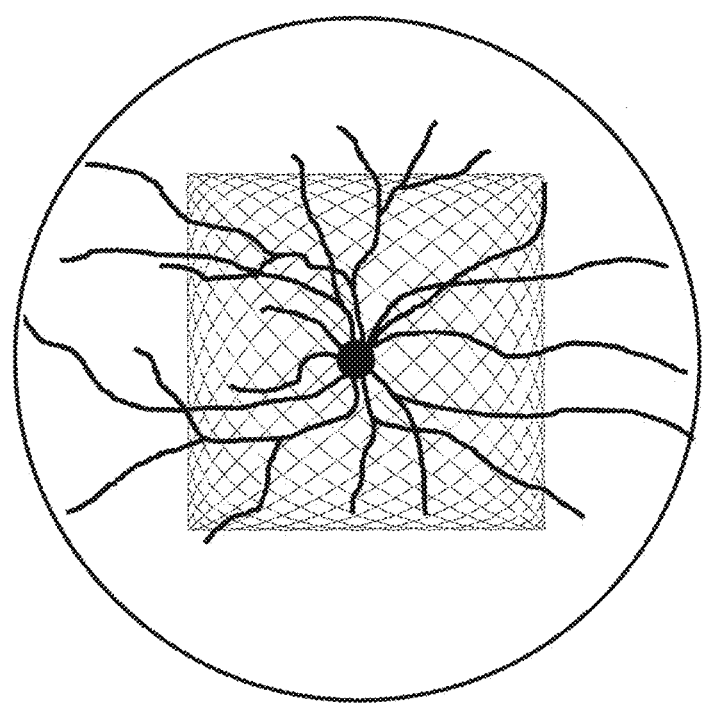
FIG. 6B is a schematic diagram showing a conventional Lissajous scan compared with an example of an OCT scan executed by the scanning imaging apparatus (ophthalmic apparatus) according to the embodiment example.

On the other hand, FIG. 6B schematically shows a distribution of scan lines applied to the fundus Ef in a conventional Lissajous scan. This conventional scan line distribution corresponds to the case in which a Lissajous scan is executed in the state shown in FIG. 5A.

As is clear from the comparison between FIG. 6A and FIG. 6B, the entire scan area of the Lissajous scan of the present example shown in FIG. 6A is wider than the scan area of the conventional Lissajous scan shown in FIG. 6B. Therefore, the present example makes it possible to apply a Lissajous scan to a wider area than conventional cases. In other words, the present example makes it possible to integrate a Lissajous scan and widening of the angle of view. Further, since the present example scans a wide area by moving a scan area of a predetermined size, widening of the angle of view can be achieved without having to make the paths of Lissajous scan cycles longer than necessary. Accordingly, the present example is capable of effectively performing motion artifact correction while achieving widening of the angle of view.

A distribution of scan lines in a central region of a scan area in conventional Lissajous scans is coarser than those in other regions. In contrast, a distribution of scan lines in a central region of an entire scan area in the present example is denser than those in other regions. Here, the central region of the entire scan area corresponds to a neighborhood region of the center of a circular path or a neighborhood region of the center of the movement of the scan area. In general, considering that a site of interest (e.g., the optic nerve head, the macula) is located in the central region of a scan area, the conventional Lissajous scan decreases the scan density for the site of interest, resulting in a low image quality for the site of interest. On the contrary, the present example has an advantage that the image quality of the site of interest is improved.

The control information stored in the memory 212 is not limited to the above example. For instance, the control information may include information for performing focus control (focus control parameter).

The focus control parameter indicates a content of control for the OCT focus driver 43A. Examples of the focus control parameter include a parameter indicating a focal position of the measurement arm, a parameter indicating a movement speed of the focal position, and a parameter indicating a movement acceleration of the focal position. The parameter indicating the focal position indicates a position of the OCT focusing lens 43, for example. The parameter indicating the movement speed of the focal position indicates a movement speed of the OCT focusing lens 43, for example. The parameter indicating the movement acceleration of the focal position indicates a movement acceleration of the OCT focusing lens 43, for example. The movement speed may or may not be constant. The same applies to the movement acceleration.

With such focus control parameters, focus adjustment can be carried out according to the shape, aberration distribution or the like of the fundus Ef. Here, a typical shape of the fundus Ef is a concave shape having a deep central part and a shallow peripheral part. The focus control is executed, for example, in an interlocking manner with at least one of the scan control (iterative control of Lissajous scan) and the movement control (control of a relative movement between a scan area and the subject's eye E). The focus control is typically interlocked with the movement control. However, it is considered effective to interlock the focus control with both the scan control and the movement control if a scan area of one Lissajous scan is relatively wide, that is, if the change in depth within a scan area of one Lissajous scan is significant. By interlocking the focus control with both the scan control and the movement control, a high quality image can be obtained in which motion artifacts are corrected and which is entirely focused.

<Scan Controller 213>

The scan controller 213 controls at least the optical scanner 44 based on the scan protocol 218. The scan controller 213 may further perform control of the light source unit 101 in an interlocking manner with the control of the optical scanner 44 based on the scan protocol 218. The scan controller 213 is implemented by cooperation between hardware including a processor and scan control software including the scan protocol 218.

<Movement Controller 214>

The movement controller 214 performs control for a relative movement between a scan area and the subject's eye E based on the movement protocol 219. The movement controller 214 of the present embodiment is configured to perform at least one of control of the LCD 39 (control of fixation targets), control of the optical scanner 44, and control of the movement mechanism 150. The movement controller 214 is implemented by cooperation between hardware including a processor and movement control software including the movement protocol 219.

The main controller 211 includes a focus controller (not shown in the figures) in the case where the focus control described above is executed. The focus controller controls the OCT focus driver 43A based on the focus control parameter. The focus controller is implemented by cooperation between hardware including a processor and focus control software including the focus control parameters.

<Image Constructing Unit 220>

The image constructing unit 220 includes a processor and constructs OCT image data of the fundus Ef based on a signal (sampling data) input from the data acquisition system 130. The OCT image data construction includes noise elimination (noise reduction), filtering, and fast Fourier transform (FFT), as in conventional Fourier domain OCT (as in conventional swept source OCT). In the cases where other types of OCT methods and techniques are employed, the image constructing unit 220 executes known processing according to the employed type, to construct OCT image data.

As described above, the present embodiment applies a Lissajous scan to the fundus Ef. The image constructing unit 220 constructs three-dimensional image data of the fundus Ef, for example, by applying the image construction methods and techniques as well as the motion artifact correction methods and techniques disclosed in Non-Patent Document 1 or 2, to data acquired through the data acquisition using Lissajous scans and the sampling by the data acquisition system 130.

The image constructing unit 220 may construct an image to be displayed, by applying rendering to three-dimensional image data. Examples of applicable rendering methods and techniques include volume rendering, surface rendering, maximum intensity projection (MIP), minimum intensity projection (MinIP), and multi planar reconstruction (MPR).

The image constructing unit 220 is capable of constructing an OCT front image (enface OCT image) based on three-dimensional image data. For example, the image constructing unit 220 can construct projection data by projecting three-dimensional image data in the z direction (i.e., in the A-line direction, in the depth direction). Further, the image constructing unit 220 can construct a shadowgram by projecting partial three-dimensional image data, which is part of three-dimensional image data, in the z direction. This partial three-dimensional image data is determined, for example, by using segmentation. Segmentation is a process that identifies a partial region in an image. The segmentation in the present example can be performed in order to identify an image region corresponding to a predetermined tissue of the fundus Ef. The segmentation is performed by, for example, the image constructing unit 220 or the data processor 230.

The ophthalmic apparatus 1 may be capable of performing OCT angiography. OCT angiography is an imaging technique that constructs an image in which blood vessels are emphasized (see, for example, Japanese Unexamined Patent Application Publication (Translation of PCT Application) No. 2015-515894). Generally, tissues of eye fundus (structure of eye fundus) does not change with time, but blood flowing inside blood vessels changes with time. OCT angiography generates an image by emphasizing parts where such temporal changes exist, that is, by emphasizing blood flow signals. Note that OCT angiography is also referred to as OCT motion contrast imaging. Images acquired by OCT angiography are referred to as angiographic images, angiograms, motion contrast images, and the like.

In the case where OCT angiography is performed, the ophthalmic apparatus 1 iteratively scans the same region of the fundus Ef a predetermined number of times. For example, the ophthalmic apparatus 1 iteratively performs the combination of the above-described scan control (iterative control of Lissajous scan) and movement control (control of a relative movement between a scan area and the subject's eye E) a predetermined number of times. With this, the data acquisition system 130 acquires a plurality of pieces of three-dimensional data (three-dimensional data set) corresponding to the three-dimensional region to which the OCT scan based on the combined control is applied. The image constructing unit 220 can construct a motion contrast image from the three-dimensional data set. The motion contrast image is an angiographic image in which the temporal change in the interference signals attributable to blood flows in the fundus Ef is emphasized. The angiographic image is three-dimensional angiographic image data that represents the three-dimensional distribution of blood vessels in the fundus Ef.

The image constructing unit 220 can construct arbitrary two-dimensional angiographic image data and/or arbitrary pseudo three-dimensional angiographic image data, from the three-dimensional angiographic image data. For example, the image constructing unit 220 can construct two-dimensional angiographic image data representing an arbitrary cross section of the fundus Ef by applying multi planar reconstruction to the three-dimensional angiographic image data. Furthermore, the image constructing unit 220 can construct front angiographic image data of the fundus Ef by applying the projection image constructing method or shadowgram constructing method described above to the three-dimensional angiographic image data.

The image constructing unit 220 is implemented by cooperation between hardware including a processor and image constructing software.

<Data Processor 230>

The data processor 230 includes a processor and perform various kinds of data processing on an image of the subject's eye E. For example, the data processor 230 is implemented by cooperation between hardware including the processor and data processing software.

The data processor 230 may perform position matching (registration) between two images acquired from the fundus Ef. For example, the data processor 230 may perform registration between three-dimensional image data acquired by an OCT technique and a front image acquired by the fundus camera unit 2. The data processor 230 may perform registration between two OCT images acquired by an OCT technique. The data processor 230 may perform registration between two front images acquired by the fundus camera unit 2. The data processor 230 may apply registration to a result obtained by analyzing an OCT image, a result obtained by analyzing a front image, or other analysis results. The registration may be performed using any known methods and techniques such as feature point extraction and affine transformation.

<User Interface 240>

The user interface 240 includes the display unit 241 and the operation unit 242. The display unit 241 includes the display device 3. The operation unit 242 includes various kinds of operation devices and input devices. The user interface 240 may include a device, such as a touch panel, that has both a display function and an operation function. Some embodiments do not include at least part of the user interface 240. For example, the display device may be an external device connected to the ophthalmic apparatus 1.

<Operation>

Figure 7:
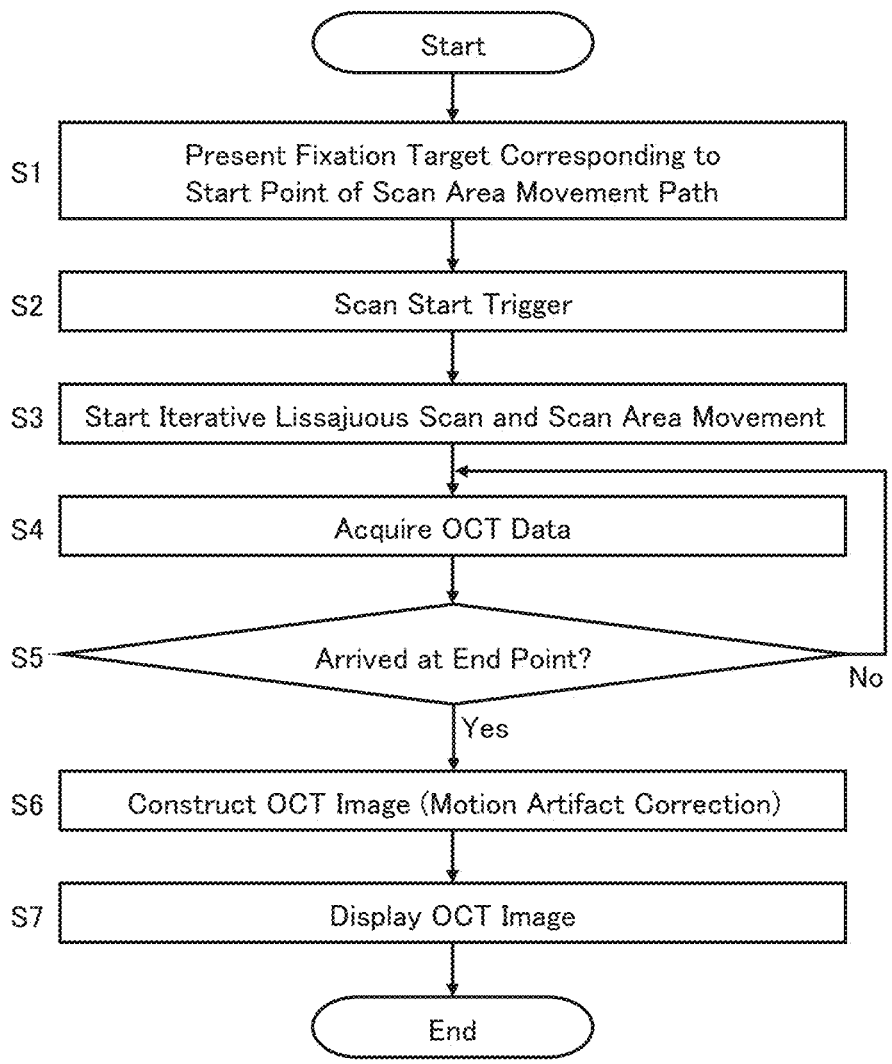
FIG. 7 is a flowchart showing an example of the operation of the scanning imaging apparatus (ophthalmic apparatus) according to the embodiment example.

The operation of the ophthalmic apparatus 1 will be described. It is assumed that preparatory processes, which are the same as conventional ones, have already been performed. The preparatory processes include input of a patient ID, setting of a scan mode, setting of a scan area movement mode, presentation of a fixation target, alignment, focus adjustment, and OCT optical path length adjustment. An example of the operation of the ophthalmic apparatus 1 will be described below with further reference to FIG. 7.

In the present example, Lissajous scan is selected as the scan mode, and movement along a circular path is selected as the scan area movement mode. The center and the radius of the circular path are assumed to be the same as those in the example shown in FIG. 5A to FIG. 5F. The same processes as in the present example may be executed in the case where another scan mode and/or another scan area movement mode are/is employed.

In the present example, the movement of the scan area is guided by changing the display position of the fixation target (fixation target image), and the movement controller 214 controls the LCD 39 (fixation target). The same processes as in the present example may be executed in the case where the scan area is moved by another element such as the optical scanner 44 or the movement mechanism 150.

(S1: Present Fixation Target Corresponding to Start Point of Scan Area Movement Path)

After the preparatory processes such as alignment are completed, the movement controller 214 controls the LCD 39 to display the fixation target at the position corresponding to the start point in the circular movement path (see, for example, FIG. 5B).

The ophthalmic apparatus 1 may be configured to execute a process for checking whether or not the subject's eye E is gazing at the fixation target, that is, whether or not an appropriate fixation state has been achieved. For example, the ophthalmic apparatus 1 may be configured to determine (assess, evaluate, judge) the fixation state by referring to an observation image of the fundus Ef obtained by the fundus camera unit 2. Alternatively, the ophthalmic apparatus 1 may be configured to display an observation image of the fundus Ef on the display unit 241 and receive a fixation state determination result from the user via the operation unit 242.

(S2: Scan Start Trigger)

Next, a trigger signal to start applying OCT scanning to the subject's eye E is generated. The trigger signal is generated in response to occurrence of any of the following events, for example: the fixation target has been displayed at the position corresponding to the start point; an appropriate fixation state has been achieved; and the user has performed a scan start instruction operation.

(S3: Start Iterative Lissajous Scan and Scan Area Movement)

When the scan start trigger of the step S2 is issued, the main controller 211 starts interlocking operation of scan control by the scan controller 213 and movement control by the movement controller 214. Here, the scan control is iterative control of Lissajous scan and the movement control is control of a relative movement between a scan area and the subject's eye E.

When the interlocking control is started, the Lissajous scan is started together with the commencement of the movement of the fixation target along the circular path, as shown in the left figure of FIG. 5C, for example. Further, the fixation target is moved as shown in FIG. 5D, FIG. 5E, and FIG. 5F. The scan area of the Lissajous scan moves as shown in FIG. 5D, FIG. 5E, and FIG.5F as a consequence of the line of sight of the subject's eye E being guided by such movement of the fixation target.

(S4: Acquire OCT Data)

OCT data acquisition is started together with the start of the OCT scan in the step S3.

(S5: Arrived at End Point?)

Both the OCT scan started in the step S3 and the OCT data acquisition started in the step S4 are continued until the movement of the scan area reaches the end point of the path (see, for example, FIG. 5F). As a result of this, the Lissajous scan is iteratively performed a predetermined number of times from the start to the end of the movement of the scan area, thereby yielding an OCT data set corresponding to the entire scan area shown in FIG. 6A, for example.

(S6: Construct OCT Image (Motion Artifact Correction))

The image constructing unit 220 constructs an OCT image from the OCT data set corresponding to the entire scan area. This process is executed according to the methods and techniques disclosed in Non-Patent Document 1 or 2, for example, and typically, motion artifact correction is also executed. As a result, three-dimensional image data corresponding to the entire scan area is obtained.

(S7: Display OCT Image)

The image constructing unit 220 applies a predetermined rendering to the three-dimensional image data constructed in the step S6. The main controller 211 displays the image constructed by the rendering on the display unit 241.

<Actions and Effects>

Some actions and effects of embodiment examples will be described.

The scanning imaging apparatus (the ophthalmic apparatus 1) according to an embodiment example includes a scanner, a scan controller, a movement unit, a movement controller, and an image constructing unit.

The scanner is configured to apply an optical scan to a sample to acquire data. In the above example, the scanner includes the OCT unit 100 and elements of the fundus camera unit 2 that form the measurement arm (e.g., the retroreflector 41, the OCT focusing lens 43, the optical scanner 44, the objective lens 22, etc.), and applies an OCT scan to the subject's eye E to acquire data.

The scan controller is configured to perform control of the scanner to sequentially apply, to the sample, a plurality of pattern scans each corresponding to a predetermined two-dimensional pattern including a series of cycles. In the above example, the scan controller includes the scan controller 213, and controls the OCT unit 100, the optical scanner 44, and the like to sequentially apply, to the subject's eye E, a plurality of Lissajous scans each corresponding to a Lissajous pattern including a series of cycles.

The movement unit is an element configured to relatively move a scan area corresponding to the two-dimensional pattern and the sample. In the above example, the movement unit includes at least one of the LCD 39, the optical scanner 44, and the movement mechanism 150, and is used to perform relative movement between the scan area corresponding to the Lissajous scan and the subject's eye E.

The movement controller is configured to perform control of the movement unit in such a manner that a cycle in a first scan of the plurality of pattern scans and a cycle in a second scan cross each other at least at one point. In the above example, the movement controller includes the movement controller 214, and controls at least one of the LCD 39, the optical scanner 44, and the movement mechanism 150 in such a manner that, for any two Lissajous scans of the plurality of Lissajous scans, an arbitrary cycle in one of the two Lissajous scans and a certain cycle in the other of the two Lissajous scans cross each other at least at one point.

The image constructing unit is configured to construct an image based on data acquired by the scanner under the control performed by the scan controller and the control performed by the movement controller. In the above example, the image constructing unit includes the image constructing unit 220, and constructs an image based on the OCT data acquired by using the OCT unit 100 etc. under the control of the scan controller 213 (iterative control of Lissajous scan) and the control of the movement controller 214 (control of a relative movement between a scan area and the subject's eye E).

Further, the scan controller and the movement controller perform the control of the scanner and the control of the movement unit respectively, in such a manner that, for each of the plurality of pattern scans, a first cycle and a second cycle in a pattern scan cross each other at least at one point. In other words, the control of the scanner by the scan controller and the control of the movement unit by the movement controller are executed in such a manner that any two cycles in each pattern scan cross each other at least at one point. In the above example, the scan controller 213 controls the OCT unit 100, the optical scanner 44, etc. and the movement controller 214 controls at least one of the LCD 39, the optical scanner 44, and the movement mechanism 150 in such a manner that, for each of the plurality of Lissajous scans, an arbitrary first cycle and a certain second cycle in a Lissajous scan cross each other at least at one point.

According to such a scanning imaging apparatus, scanning can be applied to a wider area than conventional scans since the iterative scanning and the scan area movement are combined and performed in an interlocking manner. Further, motion artifact correction can be effectively applied to data acquired from such a wide area because a wide angle of view can be achieved without having to make the cycle path longer than necessary.

Furthermore, by locating the site of interest of the sample in the central region of the scan area, a highly useful image can be obtained in which motion artifacts are appropriately corrected, the site of interest is depicted with high definition, and a wide area of the sample is depicted.

In some embodiment examples, the scanner may include a first deflector configured to deflect light in a first direction and a second direction that are mutually different. Further, the scan controller may be configured to sequentially apply the plurality of pattern scans to the sample by performing control of the first deflector in such a manner that a deflection direction change along the first direction is iterated with a first period while a deflection direction change along the second direction is iterated with a second period different from the first period.

In the above example, the first deflector includes the optical scanner 44 and is capable of deflecting light in the x direction and the y direction orthogonal to each other. The first direction and the second direction do not need to be orthogonal to each other and may only be mutually different directions. Further, the scan controller 213 is configured to apply the iterative Lissajous scan to the subject's eye E by performing control of the optical scanner 44 in such a manner that the deflection direction change along the x direction is iterated with a first period while the deflection direction change along the y direction is iterated with a second period different from the first period.

In some embodiment examples, if the sample is a living eye, the movement unit may include a fixation light projector configured to project fixation light onto the living eye. Furthermore, the movement controller may be configured to perform control of the fixation light projector to change a projection direction of the fixation light with respect to the living eye.

In the above example, the fixation light projector includes the LCD 39 (and the element group that forms the optical path from the LCD 39 to the subject's eye E). Furthermore, the movement controller 214 perform control of the LCD 39 to change the projection direction of the fixation light with respect to the subject's eye E. Note that the control for changing the projection direction of the fixation light with respect to the subject's eye E is not limited to the control of the display position of the fixation target image. For example, the change in the projection direction of the fixation light with respect to the subject's eye E may be achieved by any of the following configurations: a configuration in which a plurality of two-dimensionally arranged light emitting elements (e.g., an array of LEDs) is selectively turned on; a configuration in which a light emitting element is moved; a configuration in which a display device (e.g., LCD) is moved; and a configuration in which an element provided in the optical path from a light emitting element or a display device to the subject's eye E is controlled.

In some embodiment examples, the movement unit may include a second deflector configured to deflect light guided by the scanner. Further, the movement controller may be configured to perform control of the second deflector to change a deflection direction of the light guided by the scanner.

In the above example, the second deflector includes the optical scanner 44. The first deflector and the second deflector may be the same element or mutually different elements. Further, the movement controller 214 performs control of the optical scanner 44 to change the deflection direction of the measurement light LS guided by the measurement arm.

In some embodiment examples, the movement unit may include a movement mechanism configured to move at least part of at least the scanner. Furthermore, the movement controller may be configured to perform control of the movement mechanism to move the at least part of at least the scanner with respect to the sample.

In the above example, the movement mechanism includes the movement mechanism 150 to move the fundus camera unit 2 etc. Furthermore, the movement controller 214 performs control of the movement mechanism 150 to move the fundus camera unit 2 etc. with respect to the subject's eye E.

In some embodiment examples, the movement controller may be configured to perform the control of the movement unit to relatively move the scan area and the sample along a predetermined path. Here, the predetermined path may be a closed path. The closed path may be a circular path as in the example described above. Note that some embodiment examples may include an element for carrying out path selection from a plurality of paths. Some embodiment examples may include an element for the user to set a desired path.

In some embodiment examples, the movement controller may be configured to perform the control of the movement unit to perform the relative movement between the scan area and the sample in a continuous or stepwise manner. The above example provides an example of the continuous movement control. The stepwise movement control is implemented by, for example, a combination of sequential application of a plurality of fixation positions set in advance and application of a Lissajous scan at each fixation position (the fixation target at each fixation position is stationary).

In some embodiment examples, the movement controller may be configured to perform the control of the movement unit in such a manner that a cycle in the first scan and a cycle in the second scan cross each other at least at two points. Further, as in the above example, the movement controller may be configured to perform the control of the movement unit such that a cycle in the first scan and a cycle in the second scan cross each other at least at four points. In other words, some embodiment examples may be configured in a manner that two cycles from two mutually different pattern scans cross each other at two or more points (further, at four or more points). As a result of such configurations, motion artifact correction can be performed in a more effective manner (see for example, Non-Patent Document 1 or 2).

In some embodiment examples, the scan controller and the movement controller perform the control of the scanner and the control of the movement unit respectively in such a manner that, for each of the plurality of pattern scans, a first cycle and a second cycle in a pattern scan cross each other at least at two points. That is, some embodiment examples may be configured in a manner that cycles in the same pattern scan cross each other at two or more points. For example, as in the above example, the scan controller may be configured to perform the control of the scanner based on a scan protocol generated based on a Lissajous function in advance.

Some embodiment examples provide a method of controlling a scanning imaging apparatus. As in the above example, the scanning imaging apparatus includes a scanner that applies an optical scan to a sample to acquire data, a movement unit that relatively moves the sample and an area to which the optical scan is applied (scan area), and an image constructing unit that constructs an image based on the data acquired by the scanner.

The control method includes a scan control step, a movement control step, an interlocking control step, and an image construction step. The scan control step performs control of the scanner to sequentially apply, to the sample, a plurality of pattern scans each corresponding to a predetermined two-dimensional pattern including a series of cycles. The movement control step performs control of the movement unit in such a manner that a cycle in a first scan of the plurality of pattern scans and a cycle in a second scan cross each other at least at one point. The interlocking control step performs control of the scanner and the movement unit in such a manner that, for each of the plurality of pattern scans, a first cycle and a second cycle in a pattern scan cross each other at least at one point. The image construction step constructs an image, based on data acquired by the scanner during (under, in parallel with, simultaneously with) the control of the scanner and the control of the movement unit.

Any of the items or matters described in the embodiment example may be combined with such a control method of the scanning imaging apparatus.

Some embodiment examples provide a program that causes a computer to execute such a control method. Any of the items or matters described in the embodiment example can be combined with the program.

Some embodiment examples provide a computer-readable non-transitory recording medium storing such a program. Any of the items or matters described in the embodiment example can be combined with the recording medium. Further, the non-transitory recording medium may be in any form, and examples thereof include a magnetic disk, an optical disk, a magneto-optical disk, a semiconductor memory and the like.

According to such a control method of the scanning imaging apparatus, program, or recording medium, motion artifact correction can be effectively applied to data acquired from a wide area. Furthermore, by locating the site of interest of the sample in the central region of the scan area, a highly useful image can be obtained in which motion artifacts are appropriately corrected, the site of interest is depicted with high definition, and a wide area of the sample is depicted.

Some embodiment examples provide an imaging method. The imaging method constructs an image based on data acquired by applying an optical scan to a sample and includes the following steps. The first step is to sequentially apply, to the sample, a plurality of pattern scans each corresponding to a predetermined two-dimensional pattern including a series of cycles. The second step is to relatively move the sample and an area to which the optical scan is applied in such a manner that a cycle in a first scan of the plurality of pattern scans and a cycle in a second scan cross each other at least at one point. The third step is to perform sequential application of the plurality of pattern scans and relative movement between the area and the sample in such a manner that, for each of the plurality of pattern scans, a first cycle and a second cycle in a pattern scan cross each other at least at one point. The fourth step is to acquire data by applying an optical scan to the sample in parallel with the sequential application of the plurality of pattern scans and the relative movement of the area and the sample. The fifth step is to construct an image based on the data acquired.

Any of the items or matters described in the embodiment example may be combined with such an imaging method.

Some embodiment examples provide a program that causes a computer to execute such an imaging method. Any of the items or matters described in the embodiment example can be combined with the program.

Some embodiment examples provide a computer-readable non-transitory recording medium storing such a program. Any of the items or matters described in the embodiment example can be combined with the recording medium. Further, the non-transitory recording medium may be in any form, and examples thereof include a magnetic disk, an optical disk, a magneto-optical disk, a semiconductor memory and the like.

According to such an imaging method, program, or recording medium, motion artifact correction can be effectively applied to data acquired from a wide area. Furthermore, by locating the site of interest of the sample in the central region of the scan area, a highly useful image can be obtained in which motion artifacts are appropriately corrected, the site of interest is depicted with high definition, and a wide area of the sample is depicted.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A scanning imaging apparatus comprising:
   a scanner configured to apply an optical scan to a sample to acquire data;
   a scan controller including a first processor and configured to perform control of the scanner to sequentially apply a plurality of pattern scans to the sample, each of the plurality of pattern scans being according to a predetermined two-dimensional pattern including a series of cycles;
   a movement unit including a liquid crystal display (LCD), an optical scanner, or a movement mechanism and configured to relatively move a scan area corresponding to the two-dimensional pattern and the sample;
   a movement controller including a second processor and configured to perform control of the movement unit, in parallel with the control of the scanning performed by the scan controller, such that a cycle in a first scan of the plurality of pattern scans and a cycle in a second scan cross each other at least at one point, a scan area of the first scan being different from a scan area of the second scan; and
   an image constructing unit including a third processor and configured to construct an image based on data acquired by the scanner under the control performed by the scan controller and the control performed by the movement controller,
   wherein the scan controller and the movement controller perform the control of the scanner and the control of the movement unit respectively in parallel with each other such that, for each of the plurality of pattern scans, a first cycle and a second cycle in a pattern scan cross each other at least at one point.

2. The scanning imaging apparatus of claim 1, wherein the scanner includes a first deflector configured to deflect light in a first direction and a second direction that are mutually different, and
   the scan controller sequentially applies the plurality of pattern scans to the sample by performing control of the first deflector such that a deflection direction change along the first direction is iterated with a first period while a deflection direction change along the second direction is iterated with a second period different from the first period.

3. The scanning imaging apparatus of claim 1, wherein the sample is a living eye,
   the movement unit includes a fixation light projector configured to project fixation light onto the living eye, and
   the movement controller performs control of the fixation light projector to change a projection direction of the fixation light with respect to the living eye.

4. The scanning imaging apparatus of claim 1, wherein the movement unit includes a second deflector configured to deflect light guided by the scanner, and
   the movement controller performs control of the second deflector to change a deflection direction of the light guided by the scanner.

5. The scanning imaging apparatus of claim 1, wherein the movement unit includes the movement mechanism configured to move at least part of at least the scanner, and
   the movement controller performs control of the movement mechanism to move the at least part of at least the scanner with respect to the sample.

6. The scanning imaging apparatus of claim 1, wherein the movement controller performs the control of the movement unit to relatively move the scan area and the sample along a predetermined path.

7. The scanning imaging apparatus of claim 6, wherein the predetermined path is a closed path.

8. The scanning imaging apparatus of claim 7, wherein the predetermined path is a circular path.

9. The scanning imaging apparatus of claim 1, wherein the movement controller performs the control of the movement unit to relatively move the scan area and the sample in a continuous or stepwise manner.

10. The scanning imaging apparatus of claim 1, wherein the movement controller performs the control of the movement unit such that the cycle in the first scan and the cycle in the second scan cross each other at least at two points.

11. The scanning imaging apparatus of claim 10, wherein the movement controller performs the control of the movement unit such that the cycle in the first scan and the cycle in the second scan cross each other at least at four points.

12. The scanning imaging apparatus of claim 1, wherein the scan controller and the movement controller perform the control of the scanner and the control of the movement unit respectively such that the first cycle and the second cycle cross each other at least at two points.

13. The scanning imaging apparatus of claim 12, wherein the scan controller performs the control of the scanner based on a scan protocol generated based on a Lissajous function in advance.

\* \* \* \* \*